(12) United States Patent
McDougald et al.

(10) Patent No.: US 6,908,620 B2
(45) Date of Patent: Jun. 21, 2005

(54) COCCIDIAL VACCINE AND METHODS OF MAKING AND USING SAME

(75) Inventors: Larry R. McDougald, Watkinsville, GA (US); Alberta L. Fuller, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/730,206

(22) Filed: Dec. 8, 2003

(65) Prior Publication Data

US 2004/0120973 A1 Jun. 24, 2004

Related U.S. Application Data

(60) Provisional application No. 60/432,298, filed on Dec. 9, 2002.

(51) Int. Cl.$^7$ ............................................. A61K 39/012
(52) U.S. Cl. ............................. 424/267.1; 424/265.1; 435/243; 435/245
(58) Field of Search ........................... 424/267.1, 265.1; 435/243, 245

(56) References Cited

U.S. PATENT DOCUMENTS

| | | | |
|---|---|---|---|
| 4,438,097 A | 3/1984 | Shirley | |
| 4,639,372 A | 1/1987 | Murray et al. | |
| 5,055,292 A | * 10/1991 | McDonald et al. | ...... 424/271.1 |
| 5,068,104 A | 11/1991 | Bhogal et al. | |
| 5,387,414 A | 2/1995 | Harwood et al. | |
| 5,602,033 A | 2/1997 | Vermeulen et al. | |
| 5,614,195 A | 3/1997 | Bumstead et al. | |
| 5,635,181 A | 6/1997 | Harwood et al. | |
| 5,637,487 A | 6/1997 | Vermeulen et al. | |
| 5,677,438 A | 10/1997 | Clarke et al. | |
| 5,709,862 A | 1/1998 | Anderson et al. | |
| 5,795,741 A | 8/1998 | Bumstead et al. | |
| 5,814,320 A | 9/1998 | Clarke et al. | |
| 5,843,722 A | 12/1998 | Bumstead et al. | |
| 5,846,527 A | 12/1998 | Miller et al. | |
| 5,885,568 A | 3/1999 | Tomley et al. | |
| 5,932,225 A | 8/1999 | Wallach et al. | |
| 6,001,363 A | 12/1999 | Tomley et al. | |
| 6,100,241 A | 8/2000 | Kok et al. | |
| 6,627,205 B2 | 9/2003 | Evans et al. | |

FOREIGN PATENT DOCUMENTS

| | | | |
|---|---|---|---|
| WO | 94/16725 | * | 8/1994 |
| WO | 96/40233 | * | 12/1996 |

OTHER PUBLICATIONS

R.B. Williams, and J. Catchpole, A new protocol for a challenge test to assess the efficacy of live anticoccidial vaccines for chickens, Vaccine, (2000) vol. 18, 1178–1185.
R. B. Williams et al. The development, efficacy, and epidemiological aspects of Paracox, a new coccidiosis vaccine for chickens, Pitman–Moore Europe Monograph, Reprinted 1994 by Mallinckrodt Veterinary Ltd., pp. 1–16.

* cited by examiner

*Primary Examiner*—Jennifer E. Graser
(74) *Attorney, Agent, or Firm*—Judy Jarecki-Black; Merial Limited

(57) ABSTRACT

The present invention relates to a vaccine for coccidiosis in chickens prepared from four attenuated *Eimeria* species: *E. acervulina, E. maxima, E. mitis* and *E. tenella*. The vaccine was similar to or superior to other anticoccidial drugs in stimulating protective immunity against coccidiosis.

13 Claims, No Drawings

COCCIDIAL VACCINE AND METHODS OF MAKING AND USING SAME

RELATED APPLICATIONS

This application claims priority to U.S. Provisional Application Ser. No. 60/432,298 entitled : "COCCIDIAL VACCINE AND METHODS OF MAKING AND USING THE SAME", filed Dec. 9, 2002, the disclosure of which is incorporated by reference in its entirety. The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the preparation of immunogenic compositions and vaccines against diseases caused by coccidia. The present invention also provides for attenuated vaccines against coccidiosis.

BACKGROUND OF THE INVENTION

Coccidiosis is a disease caused by infection with one or more of the many species of *coccidia* which is a subdivision of the phylum *Protozoa*, intracellular protozoal parasites of the subphylum Apicomplexa and the genus *Eimeria*. The genus *Eimeria* contains the species of major economic importance in domestic birds, such as chickens, ducks, geese, guinea fowl, peafowl, pheasants, pigeons and turkeys. While coccidiosis occurs in practically all kinds of birds, the parasites are host specific and each species occurs in a single or in a limited group of related hosts. On the other hand, avian hosts are known to harbor more than one species of *coccidia*. Species of *Eimeria* that cause coccidiosis in chickens include *E. acervulina, E. brunette, E. hagani, E. maxima, E. mitis, E. mivati, E. necatrix, E. praecox* and *E. tenella. E. acervulina* is one of the most common species found in the litter of broiler houses. It has a great reproductive potential and is regarded as pathogenic because it produces a marked depression in gain of body weight, higher feed conversion and it produces gross lesions in the upper small intestine.

Among domesticated birds, chickens are the most susceptible to significant economic losses from coccidiosis, although losses can also occur within turkeys, geese, ducks, and guinea fowl. Coccidiosis has also produced serious losses in pheasants and quail raised in captivity. The effects of a coccidiosis infection can take the highly visible form of devastating flock mortality, but another undesirable effect is morbidity and/or weight loss which results from infection.

During the life cycle, the *Eimeria* parasite passes through a number of stages (see, e.g., U.S. Pat. No. 6,100,241 for an overview). The life cycle begins when the chicken ingests the infectious stage, known as the sporulated oocyst, during ground feeding or by inhalation of dust. The wall of the sporulated oocyst is ruptured by a combination of mechanical grinding action and chemical action in the gizzard and intestinal tract, resulting in the release of four sporocysts. The sporocysts pass into the duodenum where they are exposed to bile and digestive enzymes resulting in the release of two sporozites per sporocyst.

The sporozoites are mobile and search for suitable host epithelium cells in order to penetrate and reproduce in them. Following infection of an epithelium cell, the parasite enters the schizont phase of its life cycle, producing from 8 to 16 to >200 merozoites per schizont. Once released from the schizont, the merozoites are free to infect further epithelium cells. After two to five of these asexual reproduction cycles, the intracellular merozoites grow into sexual forms known as the female or macrogametocyte and the male or microgametocyte. Following fertilization of the macrogametocyte by the microgametes released from the microgametocyte, a zygote is formed which creates a cyst wall about itself. The newly formed oocyst is passed out of the infected chicken with the fecal droppings.

With the correct environmental conditions of temperature and humidity and sufficient oxygen in the air, the oocyst will sporulate into the infectious stage, ready to infect a new host and thereby spreading the disease. Thus, no intermediate host is required for transfer of the parasite from bird to bird.

The result of the *Eimeria* parasite infecting the digestive tract of a chicken may be a reduction in weight gain, increased feed conversion, cessation of egg production and, in some cases, death. The increase in intensive production of poultry has been accompanied by severe losses due to this parasite; indeed, coccidiosis has become an economically important parasitic disease.

In the past, several methods have been used in attempts to control coccidiosis. Prior to the advent of chemotherapeutic agents, improved sanitation using disinfectants, together with the mechanical removal of litter, was the main method employed; sufficient oocysts, however, usually remained to transmit the disease. The introduction of coccidiostatic agents in the feed or drinking water, in addition to good management, resulted in some success at disease control. Such agents have been found to suffer from a drop in effectiveness over the years, due partly to the development of drug resistant strains of coccidia. Furthermore, several chemotherapeutic agents have been found to leave residues in the meat, making it unsuitable for consumption.

U.S. Pat. Nos. 4,438,097; 4,639,372; 4,808,404; 5,055,292; 5,068,104; 5,387,414; 5,602,033; 5,614,195; 5,635,181; 5,637,487; 5,674,484; 5,677,438; 5,709,862; 5,780,289; 5,795,741; 5,814,320; 5,843,722; 5,846,527; 5,885,568; 5,932,225; 6,001,363 and 6,100,241 relate to coccidiosis vaccines, including live and recombinant vaccines. However, there are problems with existing coccidiosis vaccines, such as reduced efficacy, cross-infection with other parasites (e.g., *Clostridium* spp.) and poor bird performance. Thus, there exists a need for efficacious coccidiosis vaccines with reduced or non-existent cross-infection that do not adversely affect bird performance.

Citation or identification of any document in this application is not an admission that such document is available as prior art to the present invention.

SUMMARY OF THE INVENTION

This invention is based, in part, on an attenuated coccidiosis vaccine that is efficacious in the face of virulent challenge, reduced cross-infection with *Clostridium* spp. and has better bird performance as defined by feed conversion rates when compared to other coccidiosis vaccines.

The invention relates to a mixture of sporulated oocysts from precocious strains of *E. acervulina, E. maxima, E. mitis* and *E. tenella*. Sporulated oocysts were isolated from a seed culture harvested from one or more chickens seeded with a culture of a precocious strain of *E. acervulina, E. maxima, E. mitis* or *E. tenella*, i.e., one or more chickens are seeded with either a precocious strain of *E. acervulina, E. maxima, E. mitis* or *E. tenella* resulting in four groups of chickens, each seeded with a different *Eimeria* strain. The isolated sporulated oocysts were combined to formulate a mixture of sporulated oocysts from precocious strains of *E. acervulina, E. maxima, E. mitis* and *E. tenella*.

In an advantageous embodiment, the chickens are 2 to 8 week old SPF chickens. In another advantageous embodiment, about 100 to about 15,000 oocytes are seeded per chicken to generate the seed culture. In another advantageous embodiment, the sporulated oocysts from the seed culture are isolated by centrifugation.

The present invention also provides for verifying the sporulated oocysts are characteristic of the precocious strain of *E. acervulina, E. maxima, E. mitis* or *E. tenella*.

The invention relates to a mixture of sporulated oocysts from precocious strains of *E. acervulina, E. maxima, E. mitis* and *E. tenella*, wherein the mixture is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the mixture is about 500 oocysts of *E. acervulina*, about 50 to about 100 oocysts of *E. maxima*, about 500 oocysts of *E. mitis* and about 100 to about 500 oocysts of *E. tenella*. More advantageously, the mixture is about 500 oocysts of *E. acervulina*, about 100 oocysts of *E. maxima*, about 500 oocysts of *E. mitis* and about 100 oocysts of *E. tenella* are combined.

The invention also relates to specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

The invention also relates to testing the efficacy of the mixture of sporulated oocysts from precocious strains of *E. acervulina, E. maxima, E. mitis* and *E. tenella*. Advantageously, the testing relates to administering a challenge dose of about 100,000 to about 500,000 oocysts of *E. acervulina* and about 10,000 to about 100,000 oocysts of *E. maxima*, about 100,000 to about 500,000 oocysts of *E. mitis*, or about 10,000 to about 100,000 oocysts of *E. tenella* to the animal. In a more advantageous embodiment, the challenge dose is about 200,000 oocysts of *E. acervulina* and about 20,000 to about 50,000 oocysts of *E. maxima*, about 200,000 oocysts of *E. mitis*, or about 20,000 to about 50,000 oocysts of *E. tenella*.

The present invention relates to immunizing a chicken, advantageously a broiler chicken. However, methods of making the vaccine described herein can be extrapolated to other animals infected by *Eimeria*, in particular avians such as, but not limited to, a chicken, duck, goose, guinea fowl, peafowl, pheasant, pigeon, quail or turkey.

The invention encompasses an immunogenic or vaccine composition comprising a mixture of sporulated oocysts isolated from precocious strains of *E. acervulina, E. maxima, E. mitis* and *E. tenella*. In an advantageous embodiment, the mixture is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the mixture is about 500 oocysts of *E. acervulina*, about 50 to about 100 oocysts of *E. maxima*, about 500 oocysts of *E. mitis* and about 100 to about 500 oocysts of *E. tenella*. More advantageously, the mixture is about 500 oocysts of *E. acervulina*, about 100 oocysts of *E. maxima*, about 500 oocysts of *E. mitis* and about 100 oocysts of *E. tenella* are combined.

The invention also relates to an immunogenic or vaccine composition comprising specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

The invention also provides eliciting an immune response or inducing an immunological or protective response comprising administering an effective amount of the immunogenic or vaccine composition comprising a mixture of sporulated oocysts isolated from precocious strains of *E. acervulina, E. maxima, E. mitis* and *E. tenella* to elicit or induce the response in an animal. Advantageously, the animal is an avian such as, but not limited to, a chicken, duck, goose, guinea fowl, peafowl, pheasant, pigeon, quail or turkey. In the most advantageous embodiment, the avian is a chicken, advantageously a broiler chicken. The method of eliciting an immune response or inducing an immunological response can also include administering an adjuvant, a cytokine or both.

Advantageously, the effective amount to elicit an immune response or induce an immunological or protective response is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the effective amount is about 500 oocysts of *E. acervulina*, about 50 to about 100 oocysts of *E. maxima*, about 500 oocysts of *E. mitis* and about 100 to about 500 oocysts of *E. tenella*. More advantageously, the effective amount is about 500 oocysts of *E. acervulina*, about 100 oocysts of *E. maxima*, about 500 oocysts of *E. mitis* and about 100 oocysts of *E. tenella* are combined. In another embodiment, the effective amount is sufficient to resist a challenge dose of about 100,000 to about 500,000 oocysts of *E. acervulina* and about 10,000 to about 100,000 oocysts of *E. maxima*, about 100,000 to about 500,000 oocysts of *E. mitis*, or about 10,000 to about 100,000 oocysts of *E. tenella* to the animal. More advantageously, the challenge dose is about 200,000 oocysts of *E. acervulina* and about 20,000 to about 50,000 oocysts of *E. maxima*, about 200,000 oocysts of *E. mitis*, or about 20,000 to about 50,000 oocysts of *E. tenella*.

The effective amount to elicit an immune response or induce an immunological or protective response can also be expressed as ratios of sporulated oocysts from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

In consideration of the prevalence and pathogenicity of various *Eimeria* species, a successful attenuated coccidiosis vaccine should contain the least number of *Eimeria* strains sufficient to elicit an immune response or induce an immunological or protective response that is non-pathogenic to the recipient of the vaccine. The present relation relates to a combination of oocysts from four specific precocious strains of *Eimeria*, i.e., *E. acervulina, E. maxima, E. mitis* and *E. tenella* that results in an efficacious and non-pathogenic vaccine. The addition of other *Eimeria* strains, such as *E. brunetti, E. necatrix* and *E. praecox* may be disadvantageous with respect to efficacy, cross-infection or pathogenicity of the vaccine. Since *E. brunetti, E. necatrix* and *E. praecox* are not necessary for the efficacy of the coccidiosis vaccine disclosed herein, it would be advantageous to exclude these strains from the vaccine of the present invention.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

This invention is based, in part, on an attenuated coccidiosis vaccine that is efficacious in the face of virulent challenge, reduced cross-infection with *Clostridium* spp. and has better bird performance as defined by feed conversion rates when compared to other coccidiosis vaccines.

The invention relates to a mixture of sporulated oocysts from precocious strains of *E. acervulina, E. maxima, E. mitis* and *E. tenella*. Sporulated oocysts were isolated from a seed culture harvested from one or more chickens seeded with a culture of a precocious strain of *E. acervulina, E. maxima, E. mitis* or *E. tenella*, i.e., one or more chickens are seeded with either a precocious strain of *E. acervulina, E. maxima, E. mitis* or *E. tenella* resulting in four groups of chickens, each seeded with a different *Eimeria* strain.

Advantageously, the *Eimeria* strain is a precocious strain. Precocious strains are derived from field species are not pathogenic when administered at the right dose. In an advantageous embodiment, the *Eimeria* strain is a precocious strain of the respective microorganism as described in Avian Pathology, 17: 305–314, 1988 entitled "*Eimeria* of American Chickens: Characteristics of Six Attenuated Strains Produced by Selection for Precocious Development, P. L. Long and Joyce K. Johnson, the disclosure of which is incorporated by reference in its entirety. Microorganisms can be attenuated by their selection for precocious development as described as described in Avian Pathology, 17: 305–314, 1988 entitled "*Eimeria* of American Chickens: Characteristics of Six Attenuated Strains Produced by Selection for Precocious Development, P. L. Long and Joyce K. Johnson, the disclosure of which is incorporated by reference in its entirety. Briefly, the microorganisms are attenuated by selecting for an earlier pre-patent period, i.e., when the oocysts first show up in the feces. Such methods are well known to one of skill in the art and constitute routine experimentation.

Stock cultures of the *Eimeria* strains for the seed cultures include, but are not limited to, the following. The parent of the *Eimeria acervulina*, obtained from T. K. Jeffers at Hess and Clark Laboratories in 1969, was thought to have been isolated by Dr. M. M. Farr at USDA, Beltsville, Md., which was derived from a single oocyst. The *Eimeria maxima* culture was derived from an interbred mixture of 10 purified isolates obtained from Georgia, Delaware, Maryland, Virginia and Texas. The parent of the *Eimeria mitis* culture was isolated from Gainesville, Ga. in July 1978 and was purified by single oocyst isolation. The parent of the *Eimeria tenella* culture was obtained from a culture maintained at Pennsylvania State University by Dr. Patten since the early 1960's, and was acquired by the University of Georgia in 1982. Other precocious *Eimeria* strains include LS100 precocious *E. Acervulina* isolate 809–13, and LS precocious *E. mitis*, obtained from Merck Research Laboratories, which were obtained from Dr. Peter Long. Alternatively, attenuated precocious *Eimeria* lines that have been deposited as sporocysts at the European Collection of Animal Cell Cultures ("ECACC") as patent deposits (see, e.g., U.S. Pat. No. 5,055,292, the disclosure of which is incorporated by reference in its entirety) are useful stock cultures to generate the *Eimeria* seed cultures described herein. Specifically, deposits of *E. acervulina* (deposit no. ECACC 86072203), *E. maxima* (deposit nos. ECACC 86112011 and 86112012), *E. mitis* (deposit no. ECACC 86072206) and *E. tenella* (deposit no. ECACC 86072201) as described in U.S. Pat. No. 5,055,292 are useful stock cultures for the seed cultures of the present invention.

Advantageously, the microorganisms are attenuated by their selection for precocious development as described above. In another advantageous embodiment, the culture is pathogen-free. The stock cultures described above are advantageously maintained in the liquid or vapor phase of liquid nitrogen. Such methods are known to one of skill in the art.

In an advantageous embodiment, the chickens are two to eight weeks old. Sporulated oocysts are passed successively, without limitations to the passage, in chickens until the number of oocysts are sufficient to be used as seed for production. Advantageously, the cultures should not be held for longer than 12 months in order to maintain viability/infectivity.

In an advantageous embodiment, dedicated facilities are maintained for each *Eimeria* species. Advantageously, a sufficient volume of sporulated oocysts (seed) is mixed with feed or alternatively, is administered orally to provide each chicken with a minimum dose. In an advantageous embodiment, about 5000 to about 15,000 oocytes are seeded per chicken to generate the seed culture.

The sporulated oocysts from the seed culture are isolated from the bird feces, advantageously by centrifugation. In an advantageous embodiment, the harvest is as follows. Droppings are homogenized at an approximate ratio of 10% (w/v) in water. Large particles are removed by passing homogenate through screens. Solids are separated by either centrifugation, screening or by holding at 5±3° C. up to 24 hours. If solids are separated by holding at 5±3° C., they are further concentrated by centrifugation. The supernatant is discarded, and the solids are resuspended in a saturated NaCl (80% w/v) solution in water. The resulting solution is centrifuged. The oocysts are collected (removed) from the top of the liquid, and resuspended in water. Optionally, the remaining liquid is diluted to 20–40% NaCl with water and centrifuged. The pellet is then resuspended in a saturated NaCl solution and re-centrifuged, until no additional oocysts are recovered. The oocysts are washed no more than twice.

The oocysts are washed free of salt by repeated, resuspension centrifugation cycles-followed by resuspension in a 0.5% solution of sodium hypochlorite for 10 to 15 minutes. The oocysts are then washed free of the sodium hypochlorite solution by repeated (3×) centrifugation and resuspension steps. The final resuspension is made in a 2.5% aqueous solution of potassium dichromate ($K_2C_rO_7$). The oocysts were then transferred to sporulation vessels. Sporulation is facilitated by sparging the suspensions with air for a period not to exceed 72 hours at 27±3° C. Following sporulation the oocysts are held at 5±3° C. until the final product is produced.

In another embodiment, oocysts to be used in accord with the present vaccination method can be prepared by any of several methods known to those skilled in the a rt. Such methods include those described in J. F. Ryley at al., Parasitology 73:311–326, 1976, P. L. Long et al., Folia Veterinaria Latina VI#3, 201–217, 1976, and U.S. Pat. No. 6,627,205, the disclosures of which are incorporated by reference in their entireties. According to one method, commercial broiler chickens, approximately 2 weeks old, are infected with the *Eimeria* species of interest by oral gavage of an appropriate dose of sporulated oocysts. Well known procedures for collection and purification of oocysts from infected birds are then followed. For most species of *Eimeria* , feces are collected from infected birds 5–7 days post-infection, blended and filtered to remove debris, then centrifuged at a speed sufficient to pellet the remaining fecal material. The pellet is resuspended in a saturated salt solution, in which the oocysts float and most of the contaminating debris can be removed by centrifugation. The oocyst suspension is then diluted to lower the salt concentration. The oocysts are washed repeatedly to remove the salt and resuspended in potassium dichromate solution (2.5% w/v). The oocyst suspension is incubated at 29 C with shaking (e.g., 140 rpm) for approximately 72 hours to induce sporulation of the oocysts. Alternatively, the oocysts can be treated with sodium hypochlorite and then sporulated. The number of sporulated oocysts/ml is determined by direct count using a hemocytometer or McMaster slide, and the culture is stored under refrigeration until needed.

To prepare sporocysts, the potassium dichromate is removed from the oocyst suspension described above by repeated washing of the oocysts, which involves collection of oocysts by centrifugation and resuspending in deionized or distilled water. When the dichromate has been removed as judged by the lack of yellowish-orange coloration, the oocyst suspension is mixed with an equal volume of sodium hypochlorite (bleach) and incubated at room temperature for 15 minutes. The bleach is then removed by repeated washings, and the oocysts are resuspended in physiological saline or deionized water. Oocysts can be broken to release sporocysts using a variety of known techniques. For example, oocysts can be broken to release sporocysts by mixing the oocysts with glass beads of 1–4 mm diameter and shaking by hand, vortex mixer, or shaking incubator, or using a hand-held homogenizer. Unbroken oocysts and oocysts walls can be separated from the released sporocysts by differential centrifugation in 50% PERCOLL, a colloidal suspension of polyvinyl pyrrolidone coated silica particles (sold by Pharmacia Biotech) or 1 M sucrose as described in Dulski et al., Avian Diseases, 32: 235–239, 1988. The sporocysts can be used in the present vaccination method either mixed with or separated from the unbroken oocysts and oocysts walls. Advantageously, the dose of sporocysts is separated from the oocysts and oocysts walls.

In an advantageous embodiment, the specifications for an acceptable harvest of the seed culture are as follows. First, the ratio of sporulated oocysts to total oocysts was determined. Only harvests meeting or exceeding >40% sporulation are considered acceptable. Second, the size, shape and appearance of each oocyst harvest must be characteristic of the species intended to be produced. For example, parameters to be considered in characterizing the *Eimeria* species include, but are not limited to, DNA-based technologies, DNA buoyant density, enzyme variation, host and site specificity, immunological specificity, pathogenicity, prepatent period and sporulation time (see, e.g., Long & Joyner, J Protozool. 1984 November; 31(4): 535–41 and Shirley, Acta Vet Hung. 1997; 45(3): 331–47, the disclosures of which are incorporated by reference).

The isolated sporulated oocysts from the seed cultures described herein are combined to formulate a mixture of sporulated oocysts from precocious strains of *E. acervulina, E. maxima, E. mitis* and *E. tenella*. Generally, the mixture is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the range of sporulated oocysts in the mixture is about 125 to about 500 oocysts of *E. acervulina*, about 25 to about 100 oocysts of *E. maxima*, about 125 to about 500 oocysts of *E. mitis* and about 25 to about 500 oocysts of *E. tenella*. In one embodiment, a low dose is about 125 oocysts of *E. acervulina*, about 25 oocysts of *E. maxima*, about 125 oocysts of *E. mitis* and about 25 oocysts of *E. tenella*. In another embodiment, a medium dose is about 250 oocysts of *E. acervulina*, about 50 oocysts of *E. maxima*, about 250 oocysts of *E. mitis* and about 50 oocysts of *E. tenella*. In yet another embodiment, a high dose is about 500 oocysts of *E. acervulina*, about 100 oocysts of *E. maxima*, about 500 oocysts of *E. mitis* and about 100 oocysts of *E. tenella.*

The invention also relates to specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

Advantageously, the mixture is about 500 oocysts of *E. acervulina*, about 50 to about 100 oocysts of *E. maxima*, about 500 oocysts of *E. mitis* and about 100 to about 500 oocysts of *E. tenella*. In a more advantageous embodiment, the mixture is about 500 oocysts of *E. acervulina*, about 100 oocysts of *E. maxima*, about 500 oocysts of *E. mitis* and about 100 oocysts of *E. tenella.*

Advantageously, the oocysts are suspended in a preservative consisting of a 0.01M phosphate buffered saline solution containing gentamicin. In another embodiment, the oocysts are suspended in any one of a variety of preservatives or organic acids such as, but not limited to, acetic acid, citric acid, potassium dichromate or propionic acid. For example, but not by limitation, sufficient sterile, 0.01M phosphate buffered saline containing not more than 30 mcg/ml gentamicin, is used to yield 2 ml per bottle for a 2,000 dose presentation, 5 ml per bottle for a 5,000 dose presentation and 10 ml per bottle for a 10,000 dose presentation. Advantageously, the oocysts are stored in sterile, borosilicate glass vials. For example, but not by limitation, the oocysts are aseptically filled into vaccine vials with a semi-automatic or automatic dispenser, stoppers are mechanically or manually inserted and aluminum seals are placed and crimped.

In another embodiment, oocysts are suspended in sterile distilled water containing a suspending agent, for example a polysaccharide suspending agent such as a gum, e.g. xanthan gum or gum acacia, a cellulose derivative, e.g. carboxymethyl cellulose, hydroxypropyl methyl cellulose or microcrystalline cellulose, carageenan, sodium alginate, pectin or starch; a polypeptide suspending agent such as gelatin; a synthetic polymer suspending agent such as polyacrylic acid; or a silicate suspending agent such as magnesium aluminium silicate (see, e.g., U.S. Pat. No. 5,055,292, the disclosure of which is incorporated by reference in its entirety).

The present invention also provides for verifying the sporulated oocysts are characteristic of the precocious strain of *E. acervulina, E. maxima, E. mitis* or *E. tenella*. Advantageously, all oocysts are attenuated, in that they are precocious. In another advantageous embodiment, the size, shape and appearance of each oocyst harvest must be characteristic of the species intended to be produced. In yet another advantageous embodiment, the mixture of sporulated oocysts is tested for purity, extraneous pathogens, and/or deaths or severe lesions of the test animals, e.g., chickens. The characteristics of the various *Eimeria* species are fully set out by Long P. L. and Reid W. M. (1982: A Guide for the Diagnosis of Coccidiosis in Chickens; University of Georgia Research Report 404) and Joyner L. P. (1978: Identification and Diagnosis, Avian Coccidiosis, Poultry Science Symposium No. 13, British Poultry Science Ltd), the disclosures of which are incorporated by reference in their entireties.

The invention also relates to testing the efficacy of the mixture of sporulated oocysts from precocious strains of *E. acervulina, E. maxima, E. mitis* and *E. tenella*. Advantageously, the testing relates to administering a challenge dose of about 100,000 to about 500,000 oocysts of *E. acervulina* and about 10,000 to about 100,000 oocysts of *E. maxima*, about 100,000 to about 500,000 oocysts of *E. mitis*, or about 10,000 to about 100,000 oocysts of *E. tenella* to the animal. In a more advantageous embodiment, the challenge dose is about 200,000 oocysts of *E. acervulina* and about 20,000 to about 50,000 oocysts of *E. maxima*, about 200,000 oocysts of *E. mitis*, or about 20,000 to about 50,000 oocysts of *E. tenella*.

The invention further provides for determining bird performance as defined by feed conversion rates as a result of administering the the mixture of sporulated oocysts from precocious strains of *E. acervulina, E. maxima, E. mitis* and *E. tenella* to the birds. Feed conversion efficiency is defined as the as pounds of feed to produce a pound of meat. A common result is about 1.90 or 2.00. One point in feed conversion in common lingo is 0.01, which equals about 0.5% (half of a percent). If the metric system is used, the feed conversion is Kg of feed per Kg of meat, and is still proportional to the above.

The present invention relates to immunizing a chicken, advantageously a broiler chicken. However, methods of making the vaccine described herein can be extrapolated to other animals infected by *Eimeria*, in particular avians such as, but not limited to, a chicken, duck, goose, guinea fowl, peafowl, pheasant, pigeon, quail or turkey, or in a less advantageous embodiment, a rabbit.

The invention encompasses an immunogenic or vaccine composition comprising a mixture of sporulated oocysts isolated from precocious strains of *E. acervulina, E. maxima, E. mitis* and *E. tenella*. The isolated sporulated oocysts are combined to formulate a composition of sporulated oocysts from precocious strains of *E. acervulina, E. maxima, E. mitis* and *E. tenella*. Generally, the mixture is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the range of sporulated oocysts in the composition is about 125 to about 500 oocysts of *E. acervulina*, about 25 to about 100 oocysts of *E. maxima*, about 125 to about 500 oocysts of *E. mitis* and about 25 to about 250 oocysts of *E. tenella*. In one embodiment, a low dose is about 125 oocysts of *E. acervulina*, about 25 oocysts of *E. maxima*, about 125 oocysts of *E. mitis* and about 25 oocysts of *E. tenella*. In another embodiment, a medium dose is about 250 oocysts of *E. acervulina*, about 50 oocysts of *E. maxima*, about 250 oocysts of *E. mitis* and about 50 oocysts of *E. tenella*. In yet another embodiment, a high dose is about 500 oocysts of *E. acervulina*, about 100 oocysts of *E. maxima*, about 500 oocysts of *E. mitis* and about 100 oocysts of *E. tenella*.

Advantageously, the composition is about 500 oocysts of *E. acervulina*, about 50 to about 100 oocysts of *E. maxima*, about 500 oocysts of *E. mitis* and about 100 to about 500 oocysts of *E. tenella*. In a more advantageous embodiment, the composition is about 500 oocysts of *E. acervulina*, about 100 oocysts of *E. maxima*, about 500 oocysts of *E. mitis* and about 100 oocysts of *E. tenella*.

The composition also relates to specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., 10 sporocysts of *E. acervulina* to about 1 to 2 sporocysts of *E. maxima* to about 10 sporocysts of *E. mitis* to about 2 to 10 sporocysts of *E. tenella*). Advantageously, the ratio of *E. acervulina:E. maxima:E. mitis:E. tenella* is about 5:1:5:1 (i.e., 10:2:10:2).

The term of "immunogenic composition" covers herein any composition able, once it has been administered to an animal, e.g., avian, to elicit a protective immune response against the parasite or antigen or immunogen or epitope. The term of "vaccine" covers herein any composition able, once it has been administered to the animal, e.g., avian, to induce a protective immune response against the virus, or to efficaciously protect the animal against the parasitic invention.

Immunogenic compositions or vaccines according to the invention can also include the pathogen or immunogen, antigen or epitope of the pathogen and at least one immunogen, antigen or epitope of another pathogen, parasite or virus, i.e., the coccidiosis vaccine is combined with another avian vaccine. Such an immunogen, antigen or epitope may e.g. be of bacterial, or parasitic or viral origin or an inactivated or attenuated form of the pathogen, parasite or virus. The invention also comprehends kits to prepare these combination compositions, as well as methods for making these combination compositions and the use of the components of these combination compositions to prepare the combination compositions. Accordingly, the invention involves a kit for preparing the combination immunogenic or vaccine compositions of the invention; for instance, such a kit that comprises (a) an organism, pathogen or virus or antigen or epitope thereof (advantageously a pathogen as mentioned herein) and (b) an organism, pathogen or virus or immunogen, antigen or epitope thereof (advantageously a virus or immunogen, antigen or epitope thereof, but other pathogens as herein mentioned are also contemplated) that is different than (a), in separate containers, optionally in the same package, and optionally with instructions for admixture and/or administration.

Immunogenic compositions and/or vaccines according to the invention can include *Eimeria* culture or preparation (e.g., inactivated or attenuated *Eimeria* , or an immunogen or antigen or epitope thereof), and at least one immunogen, antigen or epitope of another avian pathogen (including without limitation the pathogen in inactivated or attenuated form). For avian multivalent immunogenic compositions and multivalent vaccines, the additional avian pathogen(s), as to which additional avian antigen(s) or immunogen(s) or epitope(s) thereof are included in and/or expressed by the multivalent immunogenic compositions and multivalent vaccines, are viruses, diseases, or pathogens of the Marek's disease virus (MDV) (e.g., serotypes 1 and 2, advantageously 1), Newcastle disease virus (NDV), paramyxoviruses other than Newcastle disease (PMV2 to PMV7), infectious bronchitis virus (IBV), infectious anaemia virus or chicken anemia virus (CAV), infectious laryngotracheitis virus (ILTV), infectious bursal disease virus (IBDV), encephalomyelitis virus or avian encephalomyelitis virus (AEV or avian leukosis virus ALV), virus of hemorragic enteritis of turkeys (HEV), pneumovirosis virus (TRTV), fowl plague virus (avian influenza), chicken hydropericarditis virus, avian reoviruses, coccidiosis, egg drop syndrome (EDS76), fowl pox, inclusion body hepatitis (adenovirus), lymphoproliferative disease of turkeys, reticuloendotheliosis in chickens, reticuloendotheliosis in turkeys, rotavirus enteritis, and turkey rhinotracheitis, *Clostridium* spp., *Escherichia coli, Mycoplasma gallinarum, Mycoplasma gallisepticum, Haemophilus avium, Pasteurella gallinarum, Pasteurella multocida gallicida*, and mixtures thereof. Advantageously, for MDV the immunogen is advantageously gB and/or gD, e.g., gB and gD, for NDV the immunogen is advantageously HN and/or F, e.g., HN and F; for IBDV the immunogen advantageously is VP2; for IBV the immunogen is advantageously S (more advantageously S1) and/or M and/or N, e.g., S (or S1) and M and/or N; for CAV the immunogen is advantageously VP1 and/or VP2; for ILTV the immunogen is advantageously gB and/or gD; for AEV the immunogen advantageously is env and/or gag/pro, e.g., env and gag/pro or gag/pro; for HEV the immunogen is advantageously the 100K protein and/or hexon; for TRTV the immunogen is advantageously F and/or G, and for fowl plague the immunogen is advantageously HA and/or N and/or NP, e.g., HA and N and/or NP. Thus, the invention also involves methods for making these compositions, as well as kits therefore.

An immunogenic composition or vaccine according to the invention that also comprises such an additional immunogenic component (additional immunogen, antigen or epitope) has the advantage that it induces an immune response or protection against several infections or maladies or causative agents thereof at the same time. This additional immunogenic component can be an attenuated or inactivated micro-organism, a recombinant construct or sub-units (e.g. proteins, glycoproteins, polypeptides, or epitopes). Epitope determination procedures, such as, generating overlapping peptide libraries (Hemmer et al., Immunology Today, 1998, 19 (4), 163–168), Pepscan (Geysen H. M. et al., Proc. Nat. Acad. Sci. USA, 1984, 81 (13), 3998–4002; Geysen H. M. et al., Proc. Nat. Acad. Sci. USA, 1985, 82 (1), 178–182; Van der Zee R. et al., Eur. J. Immunol., 1989, 19 (1), 43–47; Geysen H. M., Southeast Asian J. Trop. Med. Public Health, 1990, 21 (4), 523–533; Multipin Peptide Synthesis Kits de Chiron) and algorithms (De Groot A. et al., Nature Biotechnology, 1999, 17, 533–561), can be used in the practice of the invention, to determine epitopes of immunogens, antigens, polypeptides, glycoproteins and the like, without undue experimentation. From that information, one can construct nucleic acid molecules encoding such an epitope, and from that knowledge and knowledge in the art, one can construct vectors or constructs, e.g., recombinant viruses or vectors or plasmids that express immunogens, epitopes or antigens; all without undue experimentation.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description of immunization and vaccination methods, and can also be determined by the skilled artisan from this disclosure read in conjunction with the knowledge in the art, without any undue experimentation.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman et al., Proc. Natl. Acad. Sci., USA, 1996, 93, 2879–2883; WO98/16247), (3) an oil in water emulsion, such as the SPT emulsion described on p 147 of *"Vaccine Design, The Subunit and Adjuvant Approach"* published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778–780, Jun. 4, 1960.

With regard to structure, the acrylic or methacrylic acid polymers and EMA are preferably formed by basic units having the following formula:

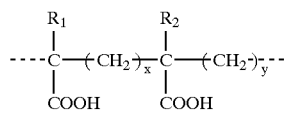

in which:
$R_1$ and $R_2$, which can be the same or different, represent H or $CH_3$
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cationic lipids (4) containing a quaternary ammonium salt which are advantageously but not exclusively suitable for plasmids, are preferably those having the following formula:

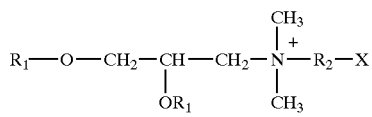

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group.

Among these cationic lipids, preference is given to DMRIE (N-(2-hydroxyethyl)-N,N-dimethyl-2,3-bis (tetradecyloxy)-1-propane ammonium; WO96/34109), preferably associated with a neutral lipid, preferably DOPE (dioleoyl-phosphatidyl-ethanol amine; Behr J. P., 1994, Bioconjugate Chemistry, 5, 382–389), to form DMRIE-DOPE.

Advantageously, the mixture with the adjuvant is formed extemporaneously and preferably contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is preferably about 95: about 5 to about 5:about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1:about 5, and preferably about 1: about 1 and about 1:about 2, e.g., 1:1 and 1:2.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFN α), interferon β (IFN β), interferon γ, (IFN γ), interleukin-1α (IL-1α), interleukin-1 β (IL-1 β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β (TNF β), and transforming growth factor β (TGF β). It is understood that cytokines can be co-administered and/or sequentially administered with the immunogenic or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to birds).

The invention also provides eliciting an immune response or inducing an immunological or protective response comprising administering an effective amount of the immunogenic or vaccine composition comprising a mixture of sporulated oocysts isolated from precocious strains of E. acervulina, E. maxima, E. mitis and E. tenella to elicit or induce the response in an animal. Advantageously, the animal is an avian such as, but not limited to, a chicken, duck, goose, guinea fowl, peafowl, pheasant, pigeon, quail or turkey. In the most advantageous embodiment, the avian is a chicken, advantageously a broiler chicken. The method of eliciting an immune response or inducing an immunological response can also include administering an adjuvant, a cytokine or both.

The effective amount to elicit an immune response or induce an immunological or protective response is about 10 to about 1000 oocysts of E. acervulina, about 10 to about 100 oocysts of E. maxima, about 10 to about 1000 oocysts of E. mitis and about 10 to about 1000 oocysts of E. tenella. Advantageously, the effective amount to elicit an immune response or induce an immunological or protective response is about 500 oocysts of E. acervulina, about 50 to about 100 oocysts of E. maxima, about 500 oocysts of E. mitis and about 100 to about 500 oocysts of E. tenella. More advantageously, the effective amount is about 500 oocysts of *E. acervulina*, about 100 oocysts of *E. maxima*, about 500 oocysts of *E. mitis* and about 100 oocysts of *E. tenella*. In another embodiment, the effective amount is sufficient to resist a challenge dose of about 100,000 to about 500,000 oocysts of *E. acervulina* and about 10,000 to about 100,000 oocysts of *E. maxima*, about 100,000 to about 500,000 oocysts of *E. mitis*, or about 10,000 to about 100,000 oocysts of *E. tenella* to the animal. More advantageously, the challenge dose is about 200,000 oocysts of *E. acervulina* and about 20,000 to about 50,000 oocysts of *E. maxima*, about 200,000 oocysts of *E. mitis*, or about 20,000 to about 50,000 oocysts of *E. tenella*.

The effective amount to elicit an immune response or induce an immunological or protective response also relates to specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

Another aspect of the present invention is a method of immunization or a method of vaccination using the immunogenic compositions or the vaccine compositions according to the invention, respectively.

The method includes at least one administration to an animal of an efficient amount of the immunogenic composition or vaccine according to the invention. The animal may be male or female. This administration may be notably done by intramuscular (IM), intradermal (ID) or subcutaneous (SC) injection or via intranasal or oral administration, wherein oral administration includes but is not limited to administration on feed or in drinking water, gels, or sprays. The immunogenic composition or the vaccine according to the invention can be administered by a syringe or a needleless apparatus (like for example Pigjet or Biojector (Bioject, Oreg., USA)). In an advantageous embodiment, the administration is oral.

The compositions according to the invention may also be administered to other mammals, e.g. mice or laboratory animal, for instance to generate polyclonal antibodies, or to prepare hybridomas for monoclonal antibodies.

The present invention provides for the immunization of animals, advantageously avians. Methods for administering coccidiosis vaccines are described in U.S. Pat. Nos. 4,438,097; 4,639,372; 4,808,404; 5,055,292; 5,068,104; 5,387,414; 5,602,033; 5,614,195; 5,635,181; 5,637,487; 5,674,484; 5,677,438; 5,709,862; 5,780,289; 5,795,741; 5,814,320; 5,843,722; 5,846,527; 5,885,568; 5,932,225; 6,001,363 and 6,100,241, the disclosures of which are incorporated by reference in their entireties. The method comprises administering to the animal an effective immunizing dose of the vaccine of the present invention. The vaccine may be administered by any of the methods well known to those skilled in the art, for example, by intramuscular, subcutaneous, intraperitoneal, intravenous, intranasally, orally, intradermal, intrabursal (just above the chickens vent), in ovo, or ocularly. Methods of administration are known to those skilled in the art. For example, U.S. Pat. Nos. 5,693,622;. 5,589,466; 5,580,859; and 5,566,064 are hereby incorporated by reference in their entirety. Birds may also be administered vaccines in a spray cabinet. Birds may also be administered the vaccine in ovo, as described in U.S. Pat. Nos. 4,458,630 and 6,627,205, the disclosures of which are incorporated by reference.

Advantageously, birds are administered vaccines in a spray cabinet, i.e., a cabinet in which the birds are placed and exposed to a vapor containing vaccine, or by course spray. In another advantageous embodiment, the immunogenic or vaccine composition is administered orally. Alternatively, the immunogenic or vaccine composition can be administered in the drinking water or the feed.

The invention encompasses an immunogenic or vaccine composition comprising a mixture of sporulated oocysts from precocious strains of *E. acervulina, E. maxima, E. mitis* and *E. tenella*. The sporulated oocysts from precocious strains of *E. acervulina, E. maxima, E. mitis* and *E. tenella* are isolated from the seed cultures described herein. Generally, the dose range of sporulated oocysts in the composition is about 10 to about 1000 oocysts of *E. acervulina*, about 10 to about 100 oocysts of *E. maxima*, about 10 to about 1000 oocysts of *E. mitis* and about 10 to about 1000 oocysts of *E. tenella*. Advantageously, the dose range of sporulated oocysts in the composition is about 125 to about 500 oocysts of *E. acervulina*, about 25 to about 100 oocysts of *E. maxima*, about 125 to about 500 oocysts of *E. mitis* and about 25 to about 500 oocysts of *E. tenella*. In one embodiment, a low dose is about 125 oocysts of *E. acervulina*, about 25 oocysts of *E. maxima*, about 125 oocysts of *E. mitis* and about 25 oocysts of *E. tenella*. In another embodiment, a medium dose is about 250 oocysts of *E. acervulina*, about 50 oocysts of *E. maxima*, about 250 oocysts of *E. mitis* and about 50 oocysts of *E. tenella*. In yet another embodiment, a high dose is about 500 oocysts of *E. acervulina*, about 100 oocysts of *E. maxima*, about 500 oocysts of *E. mitis* and about 100 oocysts of *E. tenella*.

Advantageously, the dose of the immunogenic or vaccine composition is about 500 oocysts of *E. acervulina*, about 50 to about 100 oocysts of *E. maxima*, about 500 oocysts of *E. mitis* and about 100 to about 500 oocysts of *E. tenella*. In a more advantageous embodiment, the dose is about 500 oocysts of *E. acervulina*, about 100 oocysts of *E. maxima*, about 500 oocysts of *E. mitis* and about 100 oocysts of *E. tenella*.

The invention also relates to specific ratios of sporulated oocysts isolated from precocious strains of *E. acervulina, E. maxima, E. mitis* and *E. tenella*, wherein the ratio of *E. acervulina:E. maxima:E. mitis:E. tenella* is about 10:1 to 2:10:2 to 10 (i.e., for every 10 sporocysts of *E. acervulina*, there are about 1 to 2 sporocysts of *E. maxima*, about 10 sporocysts of *E. mitis* and about 2 to 10 sporocysts of *E. tenella*). Advantageously, the ratio of *E. acervulina:E. maxima:E. mitis:E. tenella* is about 5:1:5:1 (i.e., 10:2:10:2).

Advantageously, the oocysts are suspended in a preservative consisting of a 0.01M phosphate buffered saline solution containing gentamicin. In another embodiment, the oocysts are suspended in any one of a variety of preservatives or organic acids such as, but not limited to, acetic acid, citric acid, potassium dichromate or propionic acid. For example, but not by limitation, sufficient sterile, 0.01M phosphate buffered saline containing not more than 30 mcg/ml gentamicin, is used to yield 2 ml per bottle for a 2,000 dose presentation, 5 ml per bottle for a 5,000 dose presentation and 10 ml per bottle for a 10,000 dose presentation. Advantageously, the oocysts are stored in sterile, borosilicate glass vials. For example, but not by limitation, the oocysts are aseptically filled into vaccine vials with a semi-automatic or automatic dispenser, stoppers are mechanically or manually inserted and aluminum seals are placed and crimped.

The vaccine is marketed as a multiple dose containing, 2000 dose vials, 5000 dose vials, 010,000 dose vials or 20,000 dose vials. The expiration date of the product shall not exceed 13 months from the date of the potency test initiation.

Animals, advantageously avians, can be vaccinated at any suitable age, and are usually about one to three days old before first vaccination. Advantageously, the animals are vaccinated once. Optionally, when two doses of vaccine are used, the first is normally given when the animals are 3 days to a week old and subsequently after a further 1–10 weeks dependent upon the type of animal being vaccinated.

The use, dosage and route of administration for each animal species in an advantageous embodiment is as follows. The immunogenic or vaccine composition of the present invention was used for the vaccination of healthy chickens one day of age or older, as an aid in the prevention of disease due to coccidiosis. Advantageously, the dosage was one dose per chicken by coarse water spray of 20 ml per 100 chickens.

The invention will now be further described by way of the following non-limiting examples.

EXAMPLES

Example 1

Cocci Production

Composition of the product. The microorganisms used are *Eimeria acervulina*, *Eimeria maxima*, *Eimeria mitis* and *Eimeria tenella*. The origins of the stock cultures of the microorganisms are as follows. The parent of the *Eimeria acervulina* was obtained from T. K. Jeffers at Hess and Clark Laboratories in 1969 and thought to have been isolated by Dr. M. Farr at USDA, Beltsville, Md., which was derived from a single oocyst. The *Eimeria maxima* culture was derived from an interbred mixture of 10 purified isolates obtained from Georgia, Delaware, Maryland, Virginia and Texas. The parent of the *Eimeria mitis* culture was isolated from Gainesville, Ga. in July 1978 and was purified by single oocyst isolation. The parent of the *Eimeria tenella* culture was obtained from a culture maintained at Pennsylvania State University by Dr. Patten since the early 1960's, and was acquired by the University of Georgia in 1982.

Each of the *Eimeria* strains used was a precocious strain of the respective microorganism as described in Avian Pathology, 17: 305–314, 1988 entitled "*Eimeria* of American Chickens: Characteristics of Six Attenuated Strains Produced by Selection for Precocious Development, P. L. Long and Joyce K. Johnson, the disclosure of which is incorporated by reference in its entirety. The microorganisms were attenuated by their selection for precocious development according to this method.

Cultures. Each *Eimeria* species used in the product was identified by their unique microscopic appearance, size and shape, and the zone of the chicken intestine or ceca infected, as described in Long, P. L. and W. M. Reid, A guide for the diagnosis of cocciodiosis in chickens. Re. Report 404 (Report 355 revised), Athens, Ga.: College of Agriculture Experiment Station, Univ. of Georgia; 1982, the disclosure of which is incorporated by reference in its entirety.

The microorganisms were attenuated by their selection for precocious development as described above. Each culture was free of pathogens by testing using the procedures described in 9 CFR 113.37. The stock cultures described above were maintained in the liquid or vapor phase of liquid nitrogen.

Chickens, 2 to 8 weeks of age, were used for the production of seed cultures. The route of administration was per os (i.e., orally). All seeds were sporulated oocysts and are produced in SPF chickens, 2 to 8 weeks of age. Dedicated facilities were maintained for each *Eimeria* species. A sufficient volume of sporulated oocysts (seed) was mixed with feed, free of anticoccidials, or was administered by oral gavage to provide each chicken with the minimum dose listed in Table 1. Sporulated oocysts were passed successively, without limitations to the passage, in 2 to 8 week old SPF chickens until the number of oocysts were sufficient to be used as seed for production. The cultures cannot be held for longer than 12 months in order to maintain viability/infectivity.

TABLE 1

Minimum dosage of sporulated oocysts (seed)

| species | oocysts per chicken |
| --- | --- |
| E. acervulina | 100 to 15,000 |
| E. maxima | 100 to 15,000 |
| E. mitis | 100 to 15,000 |
| E. tenella | 100 to 15,000 |

Droppings were collected daily from the third to the eighth day after inoculation. Random chickens were sacrificed and observed for characteristic infection for each species with the exception of *mitis*. No harvest was made if there was any evidence of extraneous disease.

The stock cultures for reference were maintained in liquid nitrogen. Production cultures were maintained a 5±3° C., and were passed in SPF chickens two to eight weeks of age.

The preparation of suspensions for seeding or inoculation involved serial passage of seed cultures in SPF Chickens, two to eight weeks of age, until sufficient oocysts were produced for manufacture.

A sufficient volume of sporulated oocysts (seed) was mixed with feed, free of anticoccidials, and administered to provide each chicken with the minimum dose listed in Table 1. Droppings were collected as one bath from the third to the eighth day after inoculation. Random chickens were sacrificed and observed for characteristic infection for each species with the exception of *mitis*. No harvest was made if there was any evidence of extraneous disease. The microorganisms are attenuated by their selection for precocious development as described above.

Harvest. Prior to removal of microorganisms, for production purposes, chickens were housed in a room designated for the production of individual species. The chickens were maintained on a diet free of anticocciodicals, and were allowed free access to water. Droppings were collected daily from the third to the eighth day after inoculation, and were held at 5±3° C. until processed.

The technique of harvesting microorganisms for production purposes were harvested as follows. Droppings were homogenized at an approximate ratio of 10% (w/v) in water. Large particles were removed by passing homogenate through screens. Solids were separated by either centrifugation, screening or by holding at 5±3° C. up to 24 hours. If solids were separated by holding at 5±3° C., they were further concentrated by centrifugation. The supernatant was discarded, and the solids were resuspended in a saturated NaCl (80% w/v) solution in water. The resulting solution was centrifuged. The oocysts were collected (removed) from the top of the liquid, and resuspended in water. Optimally, the remaining liquid was diluted to 20–40% NaCl with water and centrifuged. The pellet was then resuspended in a saturated NaCl solution and re-centrifuged, until no additional oocysts are recovered. The oocysts were washed no more than twice. The oocysts were washed free of salt by repeated, resuspension centrifugation cycles followed by resuspension in a 0.5% solution of sodium hypochlorite for 10 to 15 minutes. The oocysts were then washed free of the sodium hypochlorite solution by repeated (3×) centrifugation and resuspension steps. The final resuspension was made in a 2.5% aqueous solution of potassium dichromate ($K_2CrO_7$). The oocysts were then transferred to sporulation vessels. Sporulation was facilitated by sparging the suspensions with air for a period not to exceed 72 hours at 27±3° C. Following sporulation the oocysts were held at 5±3° C. until the final product was produced.

In an advantageous embodiment, the specifications for an acceptable harvest was as follows. First, the ratio of sporulated oocysts to total oocysts is determined. Only harvests meeting or exceeding >40% sporulation were considered acceptable. Second, the size, shape and appearance of each oocyst harvest must be characteristic of the species intended to be produced.

Discarded material not used in production was disposed of in a manner consistent with 9 CFR 114.15.

Preparation of the product. Serials or subserials of final product were assembled using bulk harvest fluids. All oocysts were attenuated, in that they are precocious, as described above. The oocysts were suspended in a preservative consisting of a 0.01M phosphate buffered saline solution containing not more than 30.0 mcg gentamicin. The product was standardized to yield at least the final numbers of sporulated oocyts of each species as indicated in Table 2.

TABLE 2

| Standardized dosage of sporulated oocysts | |
|---|---|
| species | oocysts per dose |
| *E. acervulina* | 500 |
| *E. maxima* | 50 |
| *E. mitis* | 500 |
| *E. tenella* | 500 |

A serial was assembled as follows. Bulk suspension lots of each of the four *Eimeria* species are removed from 5±3° C. storage and allowed to warm to ambient room temperature while stirring. A sufficient volume of each lot(s) was aseptically removed and combined, to yield not less than the oocysts per dose listed above in Table 2, as determined by calculations based on counts of each of the bulk suspensions. If necessary, multiple lots of each *Eimeria* species were combined to provide the required number of sporulated oocysts. Sufficient sterile, 0.01M phosphate buffered saline containing not more than 30 mcg/ml Gentamicin, to yield 2 ml per bottle for a 2,000 dose presentation, 5 ml per bottle was used for a 5,000 dose presentation and 10 ml per bottle for a 10,000 dose presentation. Bulk serial was maintained under constant agitation.

TABLE 3

| Example of serial volume (based on a 10,000,000 dose batch of 10,000 dose product) | |
|---|---|
| | Volume |
| *E. acervulina* | 500 ml @ $1.0 \times 10^7$ oocyts/ml |
| *E. maxima* | 300 ml @ $1.67 \times 10^6$ oocyts/ml |

TABLE 3-continued

| Example of serial volume (based on a 10,000,000 dose batch of 10,000 dose product) | |
|---|---|
| | Volume |
| *E. mitis* | 750 ml @ $6.7 \times 10^6$ oocysts/ml |
| *E. tenella* | 1050 ml @ $2.4 \times 10^6$ oocycts/ml |
| 0.01M PBS/Gentamicin | 17,400 ml |
| Total Volume | 20,000 ml |

An average 10,000-dose serial ranges from 20 L to 40 L. The fill volume is 1.0 ml per 1000 doses. The vaccine bottles are sterile, borosilicate glass vials.

The method and technique of filling and sealing final containers was as follows. The vaccine was aseptically filled into vaccine vials with a semi-automatic or automatic dispenser. Stoppers were mechanically or manually inserted. Aluminum seals are placed and crimped.

Each dose contained no less that the listed dose in Table 2 of sporulated oocysts, as calculated from bulk counts. A serial number was assigned to each quantity batched and filed in a single operation.

Testing. Each serial was tested for purity using the test methods described in 9 CFR 113.27 (e). The average count at either incubation condition should not exceed 1 colony per dose. If the average count at either incubation exceeded one colony per dose in the initial test, one retest was optionally conducted using 20 unopened final containers. If the average count at either incubation condition of the final test exceeded one colony per dose, the serial was unsatisfactory.

*Salmonella* was shown to be effectively killed by both sodium hypochlorite and by potassium dichromate, therefore, no additional testing was conducted. *Mycoplasma* was shown to be effectively killed by sodium hypochlorite, therefore, no additional testing was conducted.

Each serial was tested for extraneous pathogens in accordance with 9 CFR 113.37.

To test the safety of the vaccine, each of at least 25 one-day-old, specific pathogen free chickens was vaccinated by spray vaccination with 10 doses of vaccine. The chickens were observed each day for 21 days. Chickens that died during the period were examined and the cause of death was determined. If at least 20 chickens did not survive the observation period, the test was inconclusive. If any disease or death was directly attributable to the vaccine, the serial is unsatisfactory. Mild intestional lesions characteristic of the vaccine were considered normal, and are not considered in the safety evaluation. If less than 20 chicks survived the observation period and there were no deaths or severe lesions attributable to the vaccine, the test was optionally repeated one time. If the test is not repeated, the serial was declared unsatisfactory.

The first serial of final product produced from each new batch of production seed will be tested for potency. The product will be tested in SPF or broiler type chickens 1 to 14 days of age. Subsequent serials produced from the production seed will be evaluated for potency using preformulation counts specified above and recovery of oocysts from inoculated birds. No more that 70 chickens were used. No more than 35 were vaccinated per os with one field dose of vaccine. Twenty six to thirty days following the initial vaccination all chickens were individually identified and weights recorded. No more that 10 vaccinates and 10 controls from each of the groups listed below, were challenged per os, with 1.0 ml of each of the doses of challenge as shown in Table 4.

TABLE 4

Challenge doses

| | species | challenge dose |
|---|---|---|
| Group 1 challenge | E. acervulina | 100,000 to 500,000 oocycts |
| | E. maxima | 10,000 to 100,000 oocycts |
| Group 2 challenge | E. mitis | 100,000 to 500,000 oocysts |
| Group 3 challenge | E. tenella | 10,000 to 100,000 oocycts |

Challenge dose was also selected on the basis of pathogenicity in that the level chosen will give a minimum score of at least two.

Six days following challenge, the vaccinates and controls from each of the Groups in Table 4 w ere sacrificed, weighed, and the intestines and ceca were examined and scored for lesions. Scoring was in accordance with the Johnson and Reid cocciodial scoring system, as described in Experimental Parisitology, Vol. 28, p 30–36, 1970, the disclosure of which is incorporated by reference in its entirety, as shown in Table 5.

TABLE 5

Scoring of lesions

| score | lesion |
|---|---|
| 0 | None |
| +1 | Mild lesions |
| +2 | Moderate |
| +3 | Severe |
| +4 | Extremely severe lesions or death |

Post preparatory steps. The vaccine is marketed as a multiple dose containing, 2000 dose vials, 5000 dose vials, 010,000 dose vials or 20,000 dose vials. Collection, storage and submission of representative samples were in accordance with 9 CFR 113.3. The expiration date of the product did not exceed 13 months from the date of the potency test initiation, and confirmed in accordance with 9 CFR 114.13.

The use, dosage and route of administration for each animal species was as follows. This product was used for the vaccination of healthy chickens 1 day of age or older, as an aid in the prevention of disease due to coccidiosis. The dosage was one dose per chicken by coarse water spray; 20 ml per 100 chickens.

Example 2

Efficacy of Experimental Vaccine Containing Attenuated Strains of Avian Coccidia Compared with a Commercial Live Coccidiosis Vaccine and Salinomycin, an Anticoccidial Drug in Commercial Birds.

The objective of this Example was the determination of the efficacy of attenuated *Eimeria* oocysts vaccine, in comparison with a USDA approved live oocyst vaccine (Coccivac-B) for protection of broiler type chickens from challenge with virulent *Eimeria* species and to compare the use of the attenuated vaccine with a conventional anticoccidial drug, Salinomycin.

The target variables were as follows. The primary variable was intestinal lesion scores. Acceptance criteria was lower post-challenge intestinal coccidial lesion scores when compared to the unvaccinated, challenged control birds. Secondary variables were (1) weight gain and feed conversion during a 7-week grow-out phase and (2) mortality. Acceptance criteria included equal or superior weight gain and feed conversion in vaccinated birds vs. birds vaccinated with CoccivacB or medicated with the anticoccidial drug and low mortality in vaccinated birds vs. unvaccinated control birds, CoccivacB vaccinated birds, and anticoccidial-treated birds.

Materials. The vaccines are described in Table 6.

TABLE 6

| | Vaccines | |
|---|---|---|
| | Experimental vaccine | Coccivac |
| Scientific Name | Eimeria acervulina, E. tenella, E. maxima, E. mitis | Eimeria acervulina, E. maxima, E. tenella, E. mivati |
| Manufacturer | developed from Long's Attenuated Strains | Schering Plough |
| Formulation | Refrigerated Suspensions | |
| Preparation | Oocysts were prepared by oral inoculation of susceptible chickens, recovery of the oocysts from feces, sporulation, counting, and dilution to appropriate inoculation dose | Proprietary information |
| Expiration Date | Approximately one year | Approximately one year |
| Storage Requirements | 4°–10° C. - stored in 1.5% potassium dichromate for approximately 9 months | 4°–10° C. - stored in 1.5% potassium dichromate for approximately 9 months |
| Dose | Polyvalent inoculation with 1x vaccine, where the 1x is defined as E. tenella, 100 oocysts/bird + E. acervulina, 500 oocysts/bird + E. mitis, 500 oocysts/bird + E. maxima, 100 oocysts/bird | Proprietary info |

TABLE 6-continued

Vaccines

| | Experimental vaccine | Coccivac |
|---|---|---|
| Route of administration | Spra-Vac for oral administration | Oral administration |

TABLE 7

Virulent/Challenge Organisms

| | |
|---|---|
| Scientific Name | E. acervulina, E. mitis, E. tenella, E. maxima |
| Source | Field Isolates or Virulent Strains |
| Preparation | See Table 6 |
| Storage Requirements | See Table 6 |
| Dose | Polyvalent oral inoculation of susceptible chickens with 20,000 to 50,000 oocysts of E. tenella and E. maxima and 200,000 oocysts of E. mitis and E. acervulina |
| Route | Oral |

TABLE 8

Animals

| | |
|---|---|
| Species | Gallus domesticus (chicken) |
| Strain/breed | Commercial birds |
| Sex | F/M |
| Age | One-day |
| Number | Approximately 4000 |
| Conditioning/ acclimation | The chicks were placed in animal houses immediately after vaccination |

Animals were managed similarly and with due regard for their well-being. Animals were handled in compliance with all applicable regulations.

Experimental design. The experimental design was as follows.

TABLE 9

Experimental treatment groups

| Group | Age | Birds/ Rep | Reps/ Grp | Total Birds | Route of Admin | Inoculum | Treatment |
|---|---|---|---|---|---|---|---|
| 1 | 1 Day | 650 | 2 | 1300 | Spray* | Experimental vaccine | Once |
| 2 | 1 Day | 650 | 2 | 1300 | Spray* | Coccivac-B | Once |
| 3 | 1 Day | 650 | 2 | 1300 | N/A | Salinomycin | 60 g/ton in feed each day until Day 42 (stop on Day 28 for the birds removed for challenge) |
| 4 | 1 Day | TBD | 1 | TBD | N/A | unvaccinated | N/A |

*20 mls delivered per 100 chicks.

The timeline was as follows. On Day 0, birds were weighed by pen. The birds in Groups 1 and 2 were vaccinated as described in Table 9, with 1300 birds per vaccine regime, divided between 2 pens, one in each half of the house. The birds in Group 3 were started on Salinomycin, 60 g/ton, divided as described for Groups 1 and 2. The pens were stocked. Extra hatchmates were retained in wire cages as unvaccinated chicks.

On Day 21, the feed from starter to grower was changed for all birds. Salinomycin was continued in Group 3.

On Day 28, the birds to be challenged were moved to wire cages. Salinomycin was discontinued in Group 3 birds to be challenged. All birds and feed we weighed. Fresh fecal samples were collected from the litter from each group in the large pens, 20 samples per pen. Oocysts by quantified by species.

On Day 29, birds in the cages were challenged using the number of oocysts described in Table 7.

On Day 35, the challenge birds were terminated, the lesions were scored, and weight gains were taken.

On Day 42, all groups were changed to unmedicated finisher feed and the feed back was weighed.

On Day 49, all birds and feed were weighed and the trial was terminated.

Experimental Procedures.

Vaccination/Medication. Three treatments of birds identified as Groups 1–3 in Table 9, were replicated in half houses, three pens per house, 650 birds per pen, for a total of 1300 birds per treatment. Birds in Groups 1 through 3 were vaccinated as described in Table 9. An additional treatment group (4) was maintained separately in clean cages as unvaccinated, untreated controls, for use in the challenge test only.

Treatment Groups 1, 2, and 4 were given non-medicated feed. Treatment Group 3 was given Salinomycin (60 g/ton) beginning on Day 1 through Day 42. The birds in Group 3 to be challenged were given non-medicated feed after the move to the challenge cages. Starter feed was given until 21 days, grower until 42 days and finisher until 49 days. The feed issued was recorded, and any remaining unconsumed feed was weighed back at the time of feed changes and at termination.

Observations. Birds were weighed by pen at 0 and 28 days and by pen and sex at 49 days. Dead birds were collected twice daily and necropsy performed to determine cause of death. The fecal samples collected at Day 28 were observed for viable oocysts and quantitated by species.

Challenge. At Day 28, 3 reps of 10 birds from each pen (total of 60 per treatment) were weighed and moved to the battery cages for challenge with field strains of Eimeria (corresponding to the species used in the vaccine). All birds were given non-medicated feed in the cages. On Day 29, birds of Groups 1–4 were challenged and then terminated on Day 35. Lesion scores and weights were recorded.

The animals were randomly assigned to each treatment group by picking them up at random from the chick boxes before vaccinating. The scientists were not blind to the treatment groups since strict security was maintained between the groups to prevent cross contamination.

Concurrent Medications and Management of Adverse Events. The Coccivac vaccinated birds became sick 14 days into the trial. The diagnosis made was necrotic enteritis. The responsible agent was identified as Clostridium sordelli. All birds in the trial were administered Penicillin G to decrease contamination, and the affects thereof, between pens and to eliminate any difference in treatments among the groups that could skew the coccidiosis results.

Data Analysis.

Criteria for Measurement. The primary variables for the floor pen phase were live weights at 28 and 49 days and feed conversion at 49 days. For the challenge phase, primary variables were weight gain six days after challenge, and lesion scores of the upper, mid and cecal gut sections, also at six days after challenge.

Statistical Analysis. All statistical analyses were conducted using SAS, Cary, NC (Version 8.2). Statistical significance was based on two-tailed tests of null hypotheses that were examined in this study, resulting in p-values of 0.05 or less.

Intestinal Lesion Scores. The incidence and severity (categorical lesion scores) of post-challenge intestinal coccidial lesions were analyzed using a logit model with factors of treatment group and block and/or a survival analysis model with factors of treatment group and block (depending on the nature of the data).

Mortality. If mortality related to the virulent *Eimeria* species challenge occurred, an ANOVA (i.e., an analysis of variance) with factors of treatment group and block was conducted to determine if significant differences existed between the overall mortality means (regardless of the day of occurrence) for each treatment group.

Weight Gain and Feed Conversion.

Floor Pen Phase. Within treatment groups, paired t-tests (by block and as an entire group, without considering block effect) were conducted to determine if there are significant differences in mean live weights within each treatment group. Paired comparisons included Day 0 vs. Day 28 weights (pre-challenge) and Day 28 vs. Day 49 weights (post-challenge).

Paired t-tests (by block and as an entire group, without considering block effect) were conducted to determine if there are significant differences in mean feed conversion weights within each treatment group. Paired comparisons included Day 28 vs. Day 49 feed conversion weights (post-challenge) and Day 42 vs. Day 49 feed conversion weights (unmedicated finisher feed effect).

Between treatment groups, a repeated measures ANOVA with factors of treatment group, day, block, and group-day interaction was used to determine if significant differences existed in mean live weights between groups, on all days weights were recorded.

Challenge Phase. Within treatment groups, paired t-tests (by block and as an entire group, without considering block effect) were conducted to determine if there were significant differences in mean live weights within each treatment group. Paired comparisons included Day 28 vs. Day 35 weights (6 days post-challenge).

Between treatment groups, analysis of mean live weights between treatment groups, post-challenge, were conducted using the results of the between treatment group analysis for the floor pen phase, focusing on the Day 28 and Day 35 comparisons.

Results.

TABLE 10

28 Day Summary

| Treatments | Avg Live Wt | % Mortality (NE)* | % All Mortality | Feed Conversion |
|---|---|---|---|---|
| EXPT. VACCINE | 1.41 | 0.23 | 2.69 | 1.429 |
| COCCIVAC | 1.39 | 11.77 | 15.69 | 1.453 |
| SALINOMYCIN | 1.45 | 0.46 | 3.76 | 1.383 |

*Signifies statistical differences by grouping.

TABLE 11

49 Day Summary

| Treatments | Avg Live Male Wt | Avg Live Female Wt | Avg Total Live Wt | Feed Conversion | % Mortality NE | % Mortality Total |
|---|---|---|---|---|---|---|
| EXPT. VACCINE | 3.21 | 2.62 | 2.90 | 1.84 | 0.23 | 4.69 |
| COCCIVAC | 3.11 | 2.55 | 2.82 | 1.92 | 11.76 | 17 |
| SALINOMYCIN | 3.17 | 2.63 | 2.90 | 1.86 | 0.53 | 5.38 |

TABLE 12

Challenge Results

| Treatment | Initial Wt. | Final Wt. | 6 Day Wt. Gain | Upper Lesion Score | Middle Lesion Score | Ceca Lesion Score | TLS[1] | ATLS[2] | % Mortality Due to Coccidiosis |
|---|---|---|---|---|---|---|---|---|---|
| Negative Controls | 1425.55 ab* | 1849.72 a | 424.17 a | 0.00 c | 0.00 d | 0.00 d | 0.00 d | 0.00 d | 0 |

TABLE 12-continued

Challenge Results

| Treatment | Initial Wt. | Final Wt. | 6 Day Wt. Gain | Upper Lesion Score | Middle Lesion Score | Ceca Lesion Score | TLS[1] | ATLS[2] | % Mortality Due to Coccidiosis |
|---|---|---|---|---|---|---|---|---|---|
| Challenge Controls | 1396.95 b | 1538.75 b | 141.80 c | 2.48 a | 3.43 a | 2.38 b | 8.30 a | 2.77 a | 6.67 |
| EXPT. VACCINE | 1459.60 ab | 1777.53 a | 317.93 b | 0.78 b | 1.30 c | 2.17 b | 5.25 b | 1.42 b | 0 |
| COCCIVAC | 1469.68 a | 1851.53 a | 381.85 a | 0.85 b | 0.93 c | 0.55 c | 2.33 c | 0.78 c | 0 |
| SALINOMYCIN | 1435.47 ab | 1488.97 b | 53.50 d | 2.50 a | 2.90 b | 3.25 a | 8.65 a | 2.88 a | 0 |

60 birds were challenged per treatment.
*Signifies statistical differences by grouping.
a, b, c and d are Duncan's separation of means. (Duncan test is a statistical hoc test to separate the means).
[1] is total lesion score
[2] is average total lesion score Discussion. There were no significant differences in the lesion scores for the experimental vaccine and Coccivac for the E. maxima, E. acervulina and E. mitis challenges. Coccivac did have lower lesions scores for E. tenella as compared to the experimental strains.

It is important to note that the Coccivac vaccinated birds became infected with *Clostridium sordelli*. Clostridial disease has been linked to infection with coccidiosis in the field. Even though the infection did spread to the other treatments, the Coccivac vaccinated birds were the most affected showing 11.77% mortality.

Conclusions. The experimental *Eimeria* strains were shown to be efficacious in the face of virulent challenge. The birds vaccinated with the experimental strain had better bird performance as defined by feed conversion rates when compared to Coccivac and Salinomycin treated birds at 49 days which corresponds to a economical advantage to the poultry producer.

Having thus described in detail advantageous embodiments of the present invention, it is to be understood that the invention is not to be limited to particular details set forth in the above description as many apparent variations thereof are possible without departing from the spirit or scope of the present invention.

What is claimed is:

1. An immunogenic or vaccine composition for protection against *E. acervulina, E. maxima, E. mitis* and *E. tenella* consisting of a mixture of sporulated oocysts isolated from precocious strains of *E. acervulina, E. maxima, E. mitis* and *E. tenella*, wherein the mixture is about 500 oocysts of *E. acervulina*, about 50 to about 100 oocysts of *E. maxima*, about 500 oocysts of *E. mitis* and about 100 to about 250 oocysts of *E. tenella* combined.

2. The composition of claim 1 wherein the mixture is about 500 oocysts of *E. acervulina*, about 100 oocysts of *E. acervulina*, about 500 oocysts of *E. mitis* and about 100 oocysts of *E. tenella* combined.

3. An immunogenic or vaccine composition for protection against *E. acervulina, E. maxima, E. mitis* and *E. tenella* comprising a mixture of sporulated oocysts, wherein the mixture of sporulated oocytes consists of sporulated oocysts isolated from precocious strains of *E. acervulina, E. maxima, E. mitis* and *E. tenella*, wherein for every 10 sporocysts of *E. acervulina*, there are about 1 to 2 sporocysts of *E. acervulina*, about 10 sporocysts of *E. mitis* and about 2 to 10 sporocysts of *E. tenella*.

4. The composition of claim 3 wherein for every 10 sporocysts of *E. acervulina*, there are about 2 sporocysts of *E. maxima*, about 10 sporocysts of *E. mitis* and about 2 sporocysts of *E. tenella*.

5. A method of eliciting an immune response comprising administering an effective amount of the immunogenic or vaccine composition of claim 1 to induce the response in a chicken.

6. A method for inducing an immunological or protective response comprising administering an effective amount of the immunogenic or vaccine composition of claim 1 to induce the response in a chicken.

7. A method of eliciting an immune response comprising administering an effective amount of the immunogenic or vaccine composition of claim 3 to induce the response in a chicken.

8. A method for inducing an immunological or protective response comprising administering an effective amount of the immunogenic or vaccine composition of claim 3 to induce the response in a chicken.

9. The method of claims 5 or 6 herein the effective amount is about 500 oocysts of *E. acervulina*, about 50 to about 100 oocysts of *E. maxima*, about 500 oocysts of *E. milis* and about 100 to about 250 oocysts of *E. tenella*.

10. The method of claims 5 or 6 wherein the effective amount is about 500 oocysts of *E. acervulina*, about 100 oocysts of *E. maxima*, about 500 oocysts of *E. mitis* and about 100 oocysts of *E. tenella*.

11. The method of claims 7 or 8 wherein the effective amount of the mixture of sporulated oocysts, wherein for every 10 sporocysts of *E. acervulina*, there are about 2 sporocysts of *E. maxima* about 10 sporocysts of *E. mitis* and about 2 sporocysts of *E. tenella* in the mixture.

12. The method of any one of claims 5–8 wherein the effective amount is sufficient to resist a challenge dose of about 100,000 to about 500,000 oocysts of *E. acervulina* and about 10,000 to about 100,000 oocysts of *E. maxima*, about 100,000 to about 500,000 oocysts of *E. mitis*, or about 10,000 to about 100,000 oocysts of *E. tenella* to the animal.

13. The method of claim 12 wherein the challenge dose is about 200,000 oocysts of *E. acervulina* and about 20,000 to about 50,000 oocysts of *E. maxima*, about 200,000 oocysts of *E. mitis*, or about 20,000 to about 50,000 oocysts of *E. tenella*.

* * * * *